United States Patent [19]
Sarge et al.

[11] Patent Number: 5,995,208
[45] Date of Patent: Nov. 30, 1999

[54] INTRAVASCULAR OXIMETRY CATHETER

[75] Inventors: Jeffrey A. Sarge, Fremont; Scott T. Tsuchitani, San Francisco; Harlow B. Christianson, San Jose; Gerald G. Vurek, Mountain View; John M. Sperinde, Saratoga; Darrell H. Ogi, Sunnyvale, all of Calif.

[73] Assignee: Abbott Laboratories, Abbott Park, Ill.

[21] Appl. No.: 09/086,789

[22] Filed: May 28, 1998

[51] Int. Cl.$^6$ .................................................. G01N 33/48
[52] U.S. Cl. .................................. 356/39; 356/41; 356/42
[58] Field of Search .................................. 356/39, 41, 42

[56] References Cited

U.S. PATENT DOCUMENTS 5,342,406  8/1994  Thompson .

*Primary Examiner*—Frank G. Font
*Assistant Examiner*—Reginald A. Ratliff
*Attorney, Agent, or Firm*—Neal D. Marcus

[57] ABSTRACT

Apparatus and a method for monitoring a percentage of the oxygen saturation in the hemoglobin of blood flowing through a blood vessel. An optical sensor that detects the percentage oxygen saturation in blood is disposed proximate a proximal end of the catheter. A thermistor is disposed adjacent to the distal end of the catheter and it is employed to detect changes in blood temperature that indicate the position of the catheter's distal end in the blood vessel. Indicia or marks visible at intervals on the outer surface of the catheter enable a medical practitioner to determine the length of the catheter that has been introduced into the blood vessel. A strain relief that is flexible and resists stretching extends along the length of the catheter. For flushing the distal end of the catheter, a fluid supply may be connected to a lumen running through the catheter to provide the flushing fluid. A removable guide wire is inserted in the lumen when positioning the distal end of the catheter at a location in the blood vessel and provides enhanced rigidity for this purpose. The catheter may be coated with an anticoagulant such as heparin, to prevent blood from coagulating on the exterior surface of the catheter.

31 Claims, 7 Drawing Sheets

INTRAVASCULAR OXIMETRY CATHETER

FIELD OF THE INVENTION

The present invention generally relates to an apparatus and a method for monitoring the percentage of saturation of a substance in blood, and more specifically, to an apparatus and a method for continuously and accurately monitoring the percentage of oxygen saturation in the hemoglobin of blood flowing in a blood vessel.

BACKGROUND OF THE INVENTION

Hemoglobin is a conjugated protein that is present in all red blood cells. Red blood cells have a concave, disc shape with an approximately 10 micrometer diameter, and they commonly exist in blood vessels at densities of about five million red blood cells per cubic millimeter of blood. Also, it is well known that red blood cells both scatter and transmit light incident thereon in amounts that vary as a function of the oxygen content of the hemoglobin in the cells. The differential between absorption of light by oxygenated and non-oxygenated hemoglobin as light is transmitted through red blood cells provides a convenient basis for measuring the oxygen saturation level of the blood flowing in a blood vessel.

In the prior art, optical fiber sensors have been developed to detect and measure the amount of oxygenated hemoglobin present in the bloodstream in relation to all of the hemoglobin present in the red blood flowing through a blood vessel. The oxygen saturation level measurement is performed by utilizing an intravascular catheter that includes transmitting and receiving optical fibers for respectively conducting light to and returning light from an in vivo measurement site. The distal end of the transmitting optical fiber is commonly oriented in a co-planar relationship with the distal end of the receiving optical fiber, at the distal end of the catheter.

Light is both absorbed and back scattered by the red blood cells in the vicinity of the in vivo measurement site, with the amount of absorption varying as a function of the oxygen content of the red blood cell hemoglobin. A portion of the back scattered light enters the receiving optical fiber and is directed to an external photodetector that measures the intensity of the back scattered light. Due to the variation in radiation absorption caused by changes in the oxygen saturation of the hemoglobin in the red blood cells, the total amount of back-scattered radiant energy at the photodetector varies as a function of this oxygen saturation. For a complete description of the use of such an optical fiber sensor in an application for measurement of oxygen saturation in red blood cells, see U.S. Pat. No. 4,623,248 (Sperinde et al.), which is assigned to the assignee of the present invention.

One prospective application of an optical fiber sensor of the type described above would be to measure the continuous jugular venous oxygen saturation (SjvO2) of the blood flowing from the brain. If a cerebral (head) injury has reduced the amount of blood flowing into the skull, the brain compensates for the reduced blood flow by absorbing a greater amount of oxygen (reducing the percentage of oxygen saturation) from the available blood. Thus, the measurement of SjvO2 provides an excellent indicator of cerebral hypoxia/ischemia (reduced blood flow to the head), because it is directly linked to the amount of oxygen consumed by the brain from the available flow of blood into the skull.

In the prior art, a relatively small diameter catheter with an optical fiber sensor has been employed in attempts to measure the SjvO2 of blood exiting the head of a patient. Typically, a SjvO2 monitor is coupled to the proximal ends of a pair of optical fibers that extend longitudinally along the length of the catheter. In this prior art system, the distal ends of the optical fibers are disposed along the periphery and at the distal end of the catheter, which is adapted for disposition at a desired point in a blood vessel (vein). However, the accuracy with which SjvO2 has been measured with the prior art sensor has been disappointing. The accuracy of the sensor was found to be inconsistent, since it would at times yield measurements with unacceptable error. It was not clear what the source of the inconsistency and error could be, since the same sensor and catheter was found to provide acceptable results when used to monitor oxygen content in blood flowing through the heart. A discovery of the cause of this problem has led to the present invention.

To partially compensate for the problem, users have employed in vivo calibration of SjvO2 optical fiber sensors. Generally, the calibration is performed as follows: (1) the medical practitioner draws a blood sample through a lumen of a catheter disposed in a blood vessel; (2) a laboratory immediately measures the SjvO2 of the blood sample; (3) the medical practitioner determines the difference or offset between the laboratory's measured SjvO2 value and the SjvO2 value indicated by the optical fiber sensor; and (4) the medical practitioner compensates (increases or decreases) the SjvO2 value indicated by the optical fiber sensor with the offset determined by the calibration. However, since this compensated measurement of SjvO2 is not exact and the accuracy of the prior art SjvO2 sensor has been found to vary over time, frequent laboratory tests must be performed to verify the true SjvO2 value. Additionally, since in vivo calibration is only accurate for a specific location, the calibration must be repeated every time the disposition of the catheter is changed.

Therefore, there is a need for a catheter mounted O2 sensor to solve the problem of providing continuous and accurate percentages of the oxygen saturation of hemoglobin for blood flowing through a small diameter blood vessel, such as the jugular vein. The prior art approach of frequently calibrating such a sensor in vivo clearly does not satisfy this need.

SUMMARY OF THE INVENTION

In attempting to understand why the accuracy of determinations of the percentage of oxygen saturation in a small diameter blood vessel such as the jugular vein were inconsistent and susceptible to excessive error, it was determined that light reflected from the walls of the blood vessel (instead of from the hemoglobin in the red blood cells) adversely affects the accuracy of the percentage of oxygen saturation determination. This problem is particularly acute in smaller diameter blood vessels such as those vessels supplying blood to the brain, while in the larger vessels of the heart, the problem is generally not observed. Further, blood clotting around the distal ends of the optical fibers at the distal end of a catheter also causes an optical fiber sensor to produce inaccurate determinations of the percentage of oxygen saturation. In making SjvO2 measurements, it was found to be important to precisely position the distal end of the sensor at a specific point within the jugular vein. When using the prior art SjvO2 sensors, medical practitioners have experienced problems in determining when the catheter has been advanced to the desired point within the jugular vein. The present invention thus addresses each of these issues.

In accord with the present invention, apparatus is defined for monitoring a percentage of oxygen saturation in blood flowing through a blood vessel. The apparatus includes a flexible catheter having an elongated cylindrical shape and a diameter sufficiently small to enable the catheter to be advanced into the blood vessel as the blood is flowing through the blood vessel. A pair of optical fibers are disposed within the catheter and extend generally along the length of the catheter, from a point adjacent to the distal end of the catheter. One of the optical fibers has a proximal end coupled to a transmitter and a distal end generally disposed about a center of the distal end of the catheter. This optical fiber conveys light from the transmitter to the distal end of the catheter. Another of the optical fibers conveys reflected light and is coupled to a receiver at the proximal end of the catheter. A distal end of this optical fiber is also generally disposed about a center of the catheter, to maximize a distance between the distal end of the receiving optical fiber and a periphery of the catheter. In this manner, the reflection of light back scattered from a wall of the blood vessel, which would cause an error in the percentage of oxygen saturation sensed by the oxygen sensor, is substantially reduced.

The apparatus further comprises a thermistor disposed adjacent to the distal end of the catheter and adapted to sense a temperature of the blood flowing past the catheter. Leads disposed within the catheter are coupled to the thermistor and extend proximally from the thermistor through the catheter. Proximal ends of the leads are adapted to couple to a temperature indicator that displays a temperature of the blood flowing past the distal end of the catheter. The temperature of the blood is preferably employed to determine a relative position of the catheter within the blood vessel.

The intensity of the reflected light received at the receiver is indicative of the percentage of oxygen saturation in the blood. Specifically, the receiver is intended to receive light reflected by oxygen saturated hemoglobin in the red blood cells.

The oxygen sensor preferably includes a meter to display the percentage of oxygen saturation in the blood and may include an alarm that indicates a relationship between the percentage of oxygen saturation and a predetermined value, e.g., whether the percentage is above or below the predetermined value.

The catheter is preferably coated with an anti-clotting agent, such as heparin. In addition, it is desirable to include a strain relief member in the catheter, extending along its length. This strain relief member is flexible and resistant to longitudinal stretching. For example, the strain relief member may comprise a polymer thread.

The catheter includes a lumen extending generally along its length. A guide wire can be inserted into the lumen to make the catheter less flexible and thereby facilitate positioning the distal end of the catheter at a predetermined position in the blood vessel. When the catheter is at the predetermined position, the guide wire is retracted from the lumen. The guide wire is reinsertable into the lumen to facilitate repositioning the distal end of the catheter in the blood vessel.

A method for monitoring the percentage of oxygen saturation in blood flowing through a blood vessel is another aspect of the present invention. This method includes steps that are generally consistent with the functions provided by the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 is a schematic view of a preferred embodiment of an oximetry catheter in accord with the present invention;

FIG. 2 a cross-sectional view taken along section line 2—2 in FIG. 1, of tubing included used in the oximetry catheter;

FIG. 3 a cross-sectional view taken along section line 3—3 in FIG. 1, of a cable that includes a pair of leads for a thermistor;

DESCRIPTION OF THE PREFERRED EMBODIMENT

Figure 1:
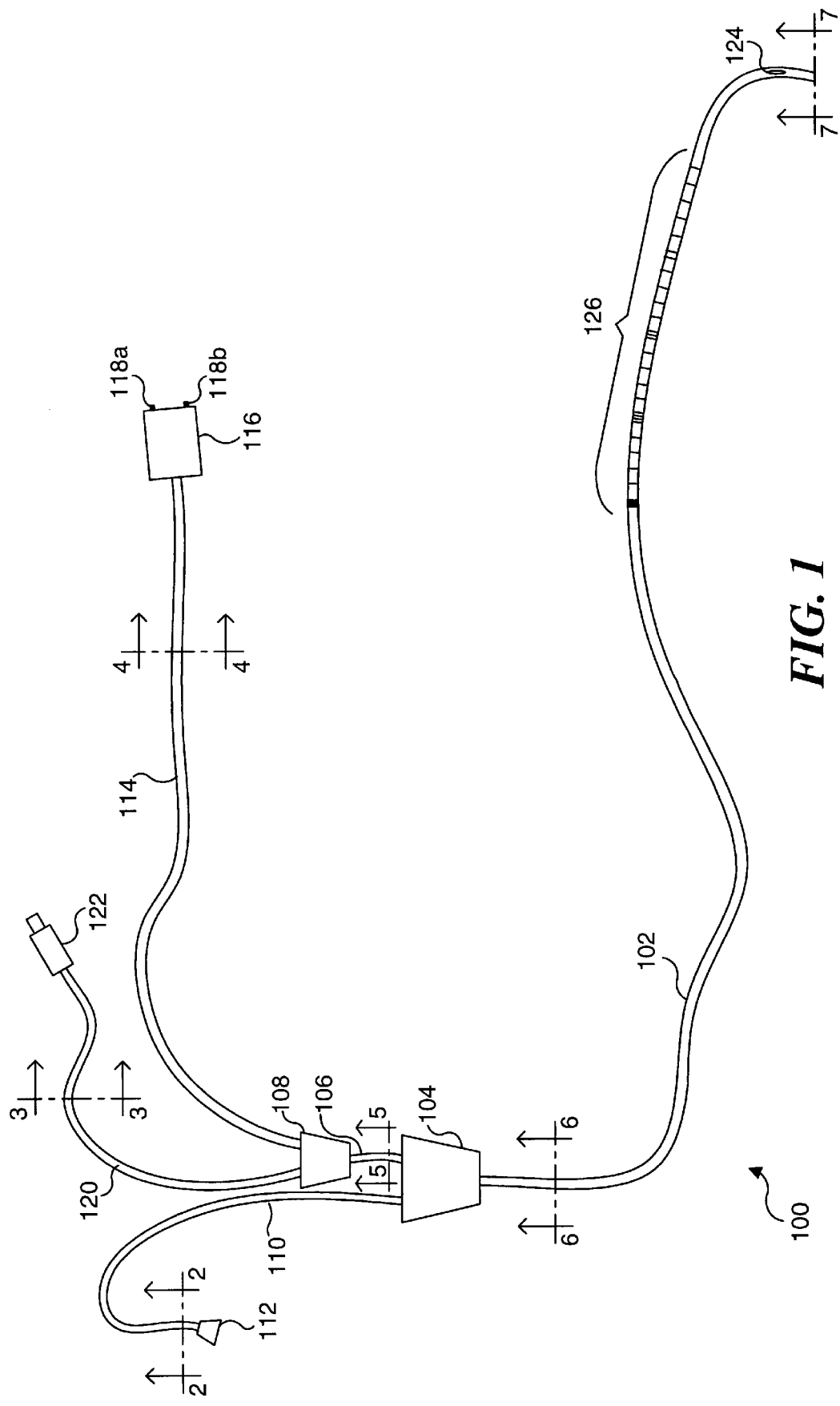

With reference to FIG. 1, a preferred embodiment 100 of the present invention includes a catheter 102, which has a distal end that is intended to be inserted into a patient's blood vessel and a proximal end that is adapted to connect a blood oxygen sensor (not shown in this Figure). At the proximal end of the catheter is a manifold 104. A proximal end of a cable 106 is coupled to manifold 104, and a distal end of the cable is coupled to a manifold 108. A fitting 112 is connected to a proximal end of tubing 110; a distal end of the tubing is coupled to manifold 104. Coupled to the proximal side of manifold 108 is a cable 120; an electrical connector 122 is connected to a proximal end of cable 120. Also coupled to the proximal side of manifold 108 is an optical cable 114. An optical connector 116 is connected to a distal end of optical cable 114, and on its proximal side, includes an optical input 118a and an optical output 118b. A plurality of indicia 126 are disposed at intervals along a distal portion of catheter 102 and serve to provide an indicator enabling a medical practitioner to determine the length of the catheter that has been introduced inside a patient's vascular system. Additionally, a port 124 is disposed substantially adjacent to a distal end of catheter 102, giving access to a lumen (not shown in this Figure) within the interior of the catheter.

Figure 2:
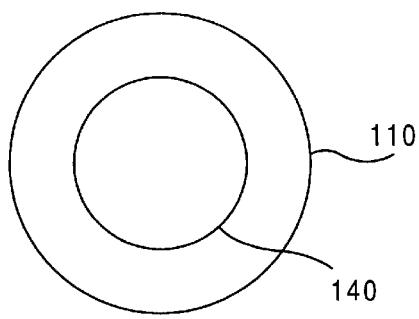

Turning to FIG. 2, a cross-sectional view of tubing 110 is depicted. As shown in this Figure, a lumen 140 extends through the interior of tubing 110 (and along its length).

Figure 3:
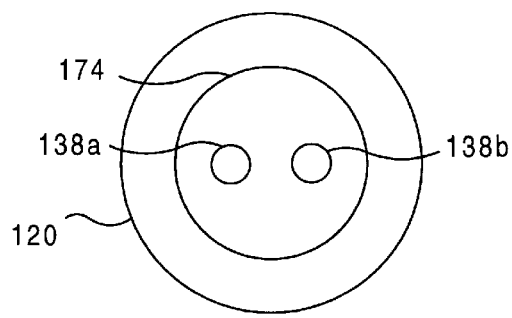

In FIG. 3, a cross-sectional view of cable 120 is illustrated. A pair of leads 138a and 138b, shown in cross section, are disposed in a lumen 174 and extend through cable 120, generally parallel with its longitudinal axis. Although not shown in this Figure, electrical connector 122 is coupled to leads 138a and 138b at the proximal end of cable 120.

Figure 4:
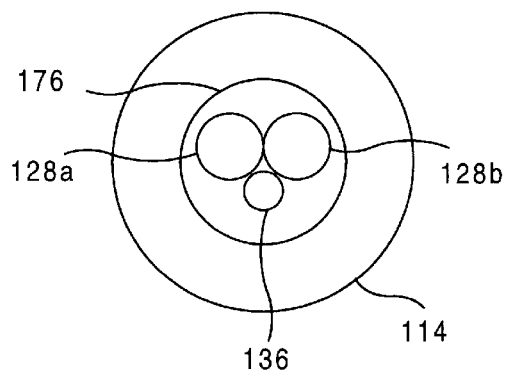
FIG. 4 is a cross-sectional view taken along section line 4—4 in FIG. 1, of a cable that includes a strain relief and a pair of optical fibers for a light sensor.

Referring now to FIG. 4, a cross-sectional view of cable 114 illustrates a pair of optical fibers 128a and 128b and a strain relief 136 that are disposed in a lumen 176, each of which extend through the cable, generally parallel to its longitudinal axis. A proximal end of optical fiber 128a is directly connected to optical input 118a (shown in FIG. 1). Similarly, a proximal end of optical fiber 128b is connected to optical output 118b (also shown in FIG. 1). Strain relief 136 will preferably comprise a flexible polymer material that is resistant to longitudinal stretching, such as a Kevlar™ thread.

Figure 5:
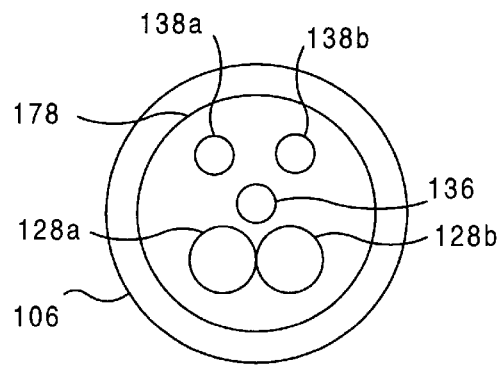
FIG. 5 is a cross-sectional view taken along section line 5—5 in FIG. 1, of a cable that includes the pair of leads, the strain relief, and the pair of optical fibers.

In FIG. 5, a cross-sectional view of cable 106 illustrates the disposition of optical fibers 128a and 128b, leads 138a and 138b, and strain relief 136. These elements extend through a lumen 178, generally parallel to the longitudinal axis of cable 106.

Figure 6:
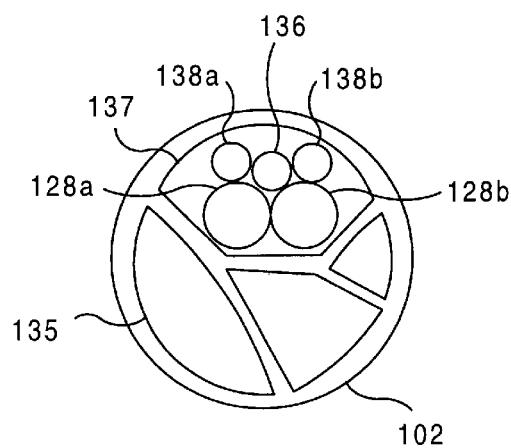
FIG. 6 is a cross-sectional view taken along section line 6—6 in FIG. 1, of the distal portion of the oximetry catheter intended for disposition in a patient's blood vessel.

Turning now to FIG. 6, a cross-sectional view of catheter 102 illustrates a lumen 135, which extends through the interior of catheter 102, generally parallel to its longitudinal axis. Also extending generally parallel to the longitudinal axis of catheter 102 is another lumen 137. Optical fibers 128a and 128b, leads 138a and 138b, and strain relief 136 are disposed within lumen 137 and extend along the length of catheter 102.

Figure 7:
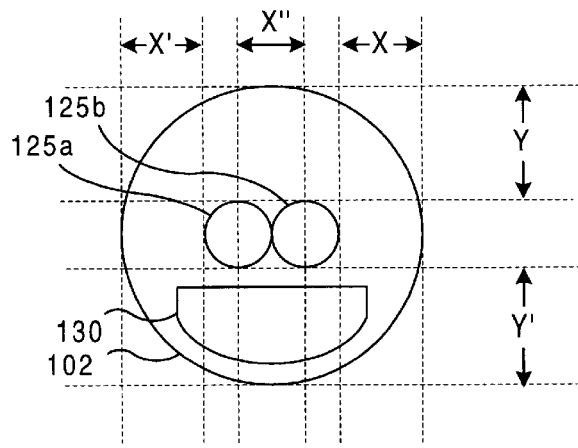
FIG. 7 is an end view taken along section line 7—7 in FIG. 1, of a distal end of the oximetry catheter.

In FIG. 7, the distal end of catheter 102 is shown. A port 130 is disposed adjacent to distal ends 125a and 125b of optical fibers 128a and 128b, respectively, and the distal ends are generally co-planar and disposed at or about a center of catheter 102 (i.e., at each side of the catheter's longitudinal center axis). Port 130 is directly coupled to lumen 135 (shown in FIG. 6). In this preferred embodiment, the cross-sectional centers of both distal end 125a and distal end 125b are each at least 0.030 inches from a periphery of catheter 102. Maintaining a sufficient distance between the external surface of the catheter and the distal ends of optical fibers 128a and 128b is very important. This distance must be sufficiently great so that any light emitted from distal end 125a and reflected from an adjacent wall of a blood vessel is too low in intensity at distal end 125b to interfere with the accuracy with which a percentage of oxygen saturation is determined in the blood. It has been found that the error in determining the percentage of oxygen saturation becomes greater as more light is reflected back into distal end 125b from the wall of a blood vessel in which the oximetry measurement is being made. Accordingly, in the exemplary preferred embodiment of the oximetry sensing system shown in the Figures, all of the indicated distances (X, X', Y, and Y' in FIG. 7) from the periphery of catheter 102 to the edge of distal end 125a and distal end 125b are preferably equal to or greater than 0.020 inches. Additionally, the indicated distance (X" in FIG. 7) between the cross-sectional centers of distal end 125a and distal end 125b are preferably within the range from 0.0095 inches to 0.0105 inches.

Figure 8:
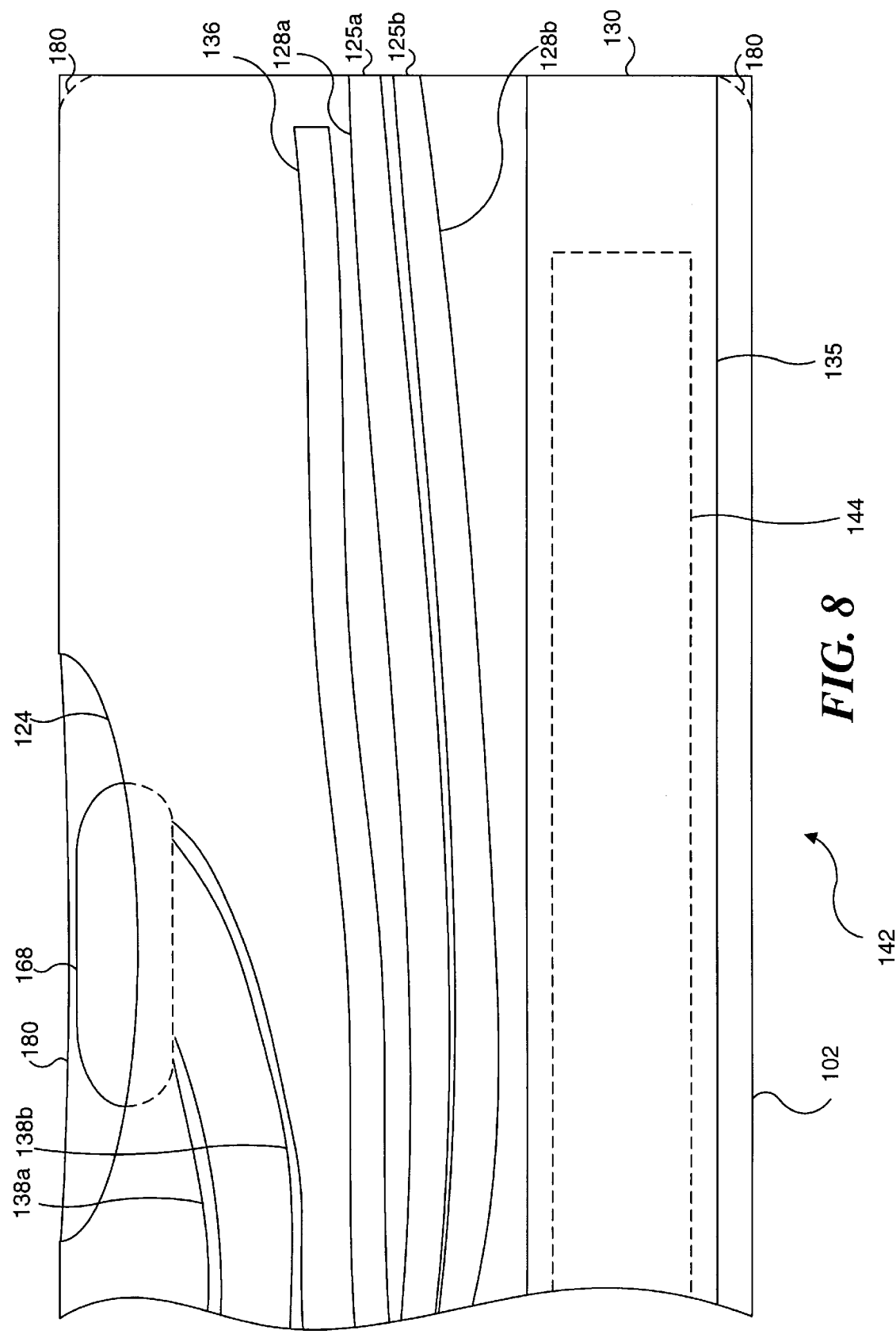
FIG. 8 is a side elevational view of a portion of the distal end of the oximetry catheter accent its distal end.

An elevational view 142 of a portion of the distal end of catheter 102 is shown in FIG. 8. In this Figure, a thermistor 168 is disposed at port 124, and leads 138a and 138b are coupled to the thermistor to convey an electrical current that flows through it. Port 124 is sealed with a fill 180 that protects thermistor 168 from mechanical damage and direct exposure to bodily fluids and tissue. In the present invention, fill 180 is composed of urethane or another biocompatible material. The conductivity of thermistor 168 is proportional to temperature, so that the electrical current conducted by leads 138a and 138b that flows through the thermistor is indicative of its temperature, and thus, of the temperature of the environment surrounding the distal end of catheter 102. Strain relief 136 extends along the length of catheter 102, within lumen 137 and generally parallel to the longitudinal axis of the catheter. When inserting the catheter into the patient's vascular system, the distal end of a guide wire 144 is positioned within lumen 135 near port 130. Although all of the details are not shown in this Figure, guide wire 144 has been inserted through fitting 112 and extends along lumen 140 into lumen 135, to the distal end of catheter 102. The disposition of guide wire 144 within catheter 102 reduces its flexibility and enables the medical practitioner to precisely position the distal end of the catheter within a blood vessel in the patient's body. Optical fibers 128a and 128b are also disposed within lumen 137, extending along the length of catheter 102, and generally parallel to its the longitudinal axis.

Figure 9:
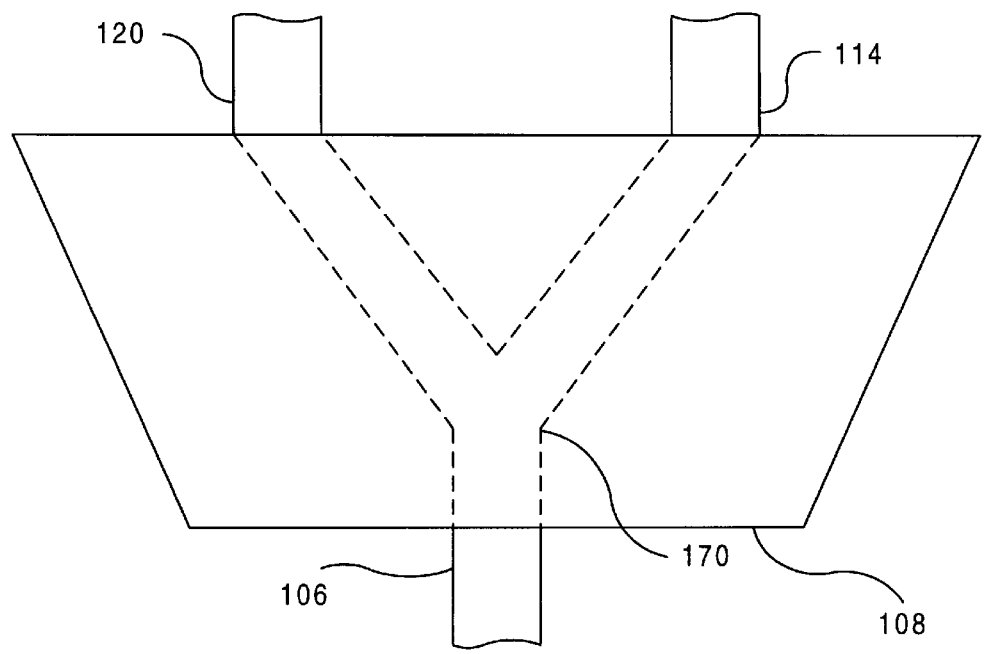
FIG. 9 is a plan view of a splitter used to combine the elements of the cable that includes the air of leads, and the cable that includes the pair of optical fibers and the strain relief filament.
Figure 10:
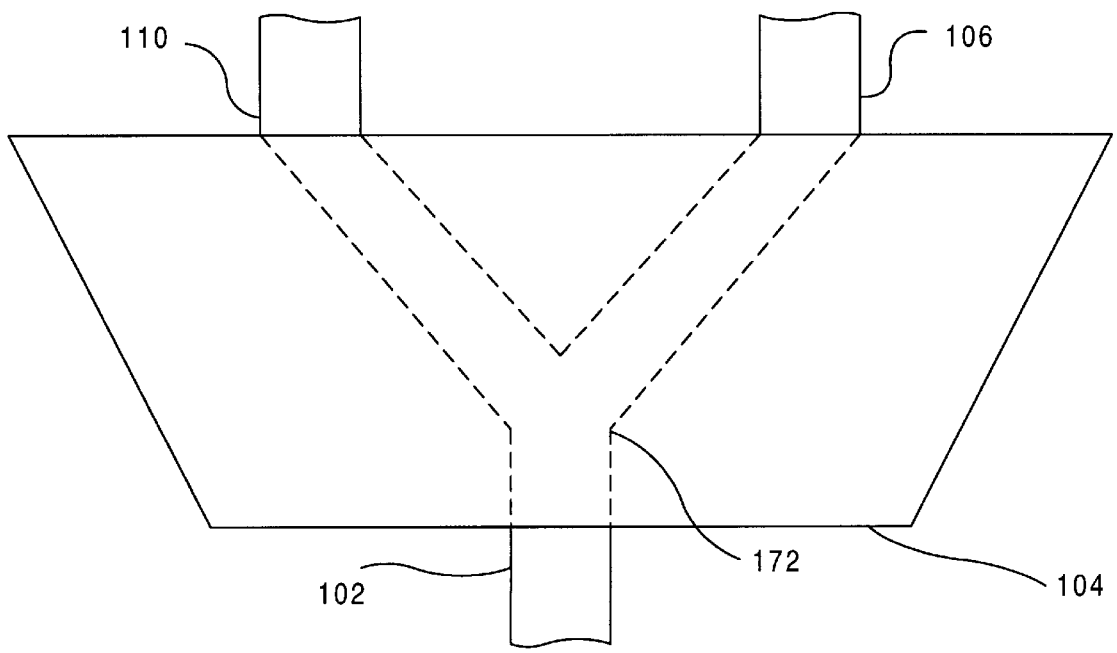
FIG. 10 is a cross-sectional plan view of a splitter used to combine the elements of the tubing, and the cable that includes the pair of leads, the pair of optical fibers, and the strain relief into the distal portion of the oximetry catheter.

As indicated in FIG. 9, manifold 108 is employed to combine the elements of cable 120 and cable 114 at a "Y" connection 170. Similarly, as indicated in FIG. 10, manifold 104 combines the elements of cable 106 and tubing 110 together into catheter 102 at a "Y" connection 172.

Figure 11:
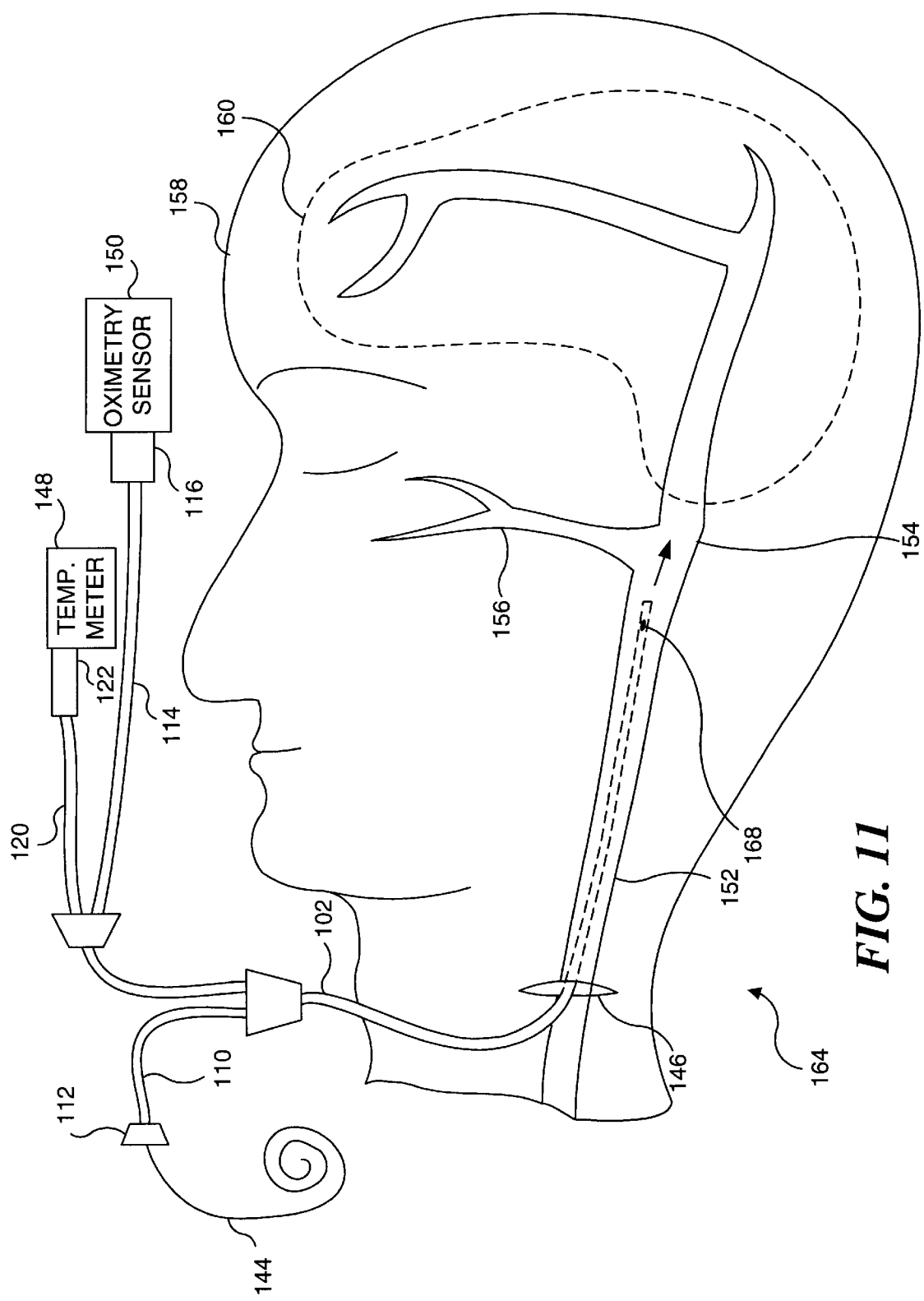
FIG. 11 is a schematic drawing illustrating the positioning of the distal portion of the oximetry catheter in the interior jugular vein of a patient.

In FIG. 11, a schematic overview 164 illustrates catheter 102 being advanced to a monitoring position in a head 158 of a patient. A portion of guide wire 144 remains coiled outside fitting 112 and another portion has been inserted through the fitting advanced along the length of lumen 140 (FIG. 2), and into a portion of lumen 135 (FIG. 6), to a point (not shown) near the distal end of the catheter. As noted above, the insertion of guide wire 144 into lumen 135 reduces the flexibility of catheter 102 and enables a medical practitioner to precisely position the distal end of the catheter within an interior jugular vein 152 through an incision 146 in the neck of the patient. A facial vein 156 is connected to interior jugular vein 152 just below a jugular bulb 154.

The venous blood temperature sensed by thermistor 168 at port 124 is slightly cooler when the distal end of catheter 102 is positioned at, or slightly below, facial vein 156. The venous blood returning from the patient's facial tissue is closer to the skin and thus, is typically cooler than blood returning from a brain 160 of the patient. A temperature meter or indicator 148 that displays the temperature of venous blood in real time is coupled through connector 122 and leads 138a and 138b to thermistor 168. The medical practitioner may thereby monitor the venous blood temperature in order to precisely position the distal end of catheter 102 in interior jugular vein 152. Additionally, an optical connector 116 is connected to an oximetry sensor 150 that employs a meter to display the percentage of oxygen saturation sensed at the distal end of catheter 102. Oximetry sensor 150 includes an optical transmitter (light source) that is coupled to optical input 118a and an optical receiver (photo detector) that is coupled to optical output 118b. The optical transmitter radiates light through optical input 118a that is emitted from distal end 125a at the distal end of the catheter 102 and the optical receiver senses the reflected (back scattered) light at distal end 125b through optical output 118b. The amount of reflected light is employed by oximetry sensor 150 to determine a percentage for the oxygen saturation of the hemoglobin in the venous blood at the distal end of catheter 102. The sensing technique used to determine the percentage of oxygen saturation of hemoglobin in the blood is disclosed in commonly assigned U.S. Pat. No. 4,623,248 (Sperinde et al.), the drawings and disclosure of which are hereby specifically incorporated herein by reference.

Figure 12:
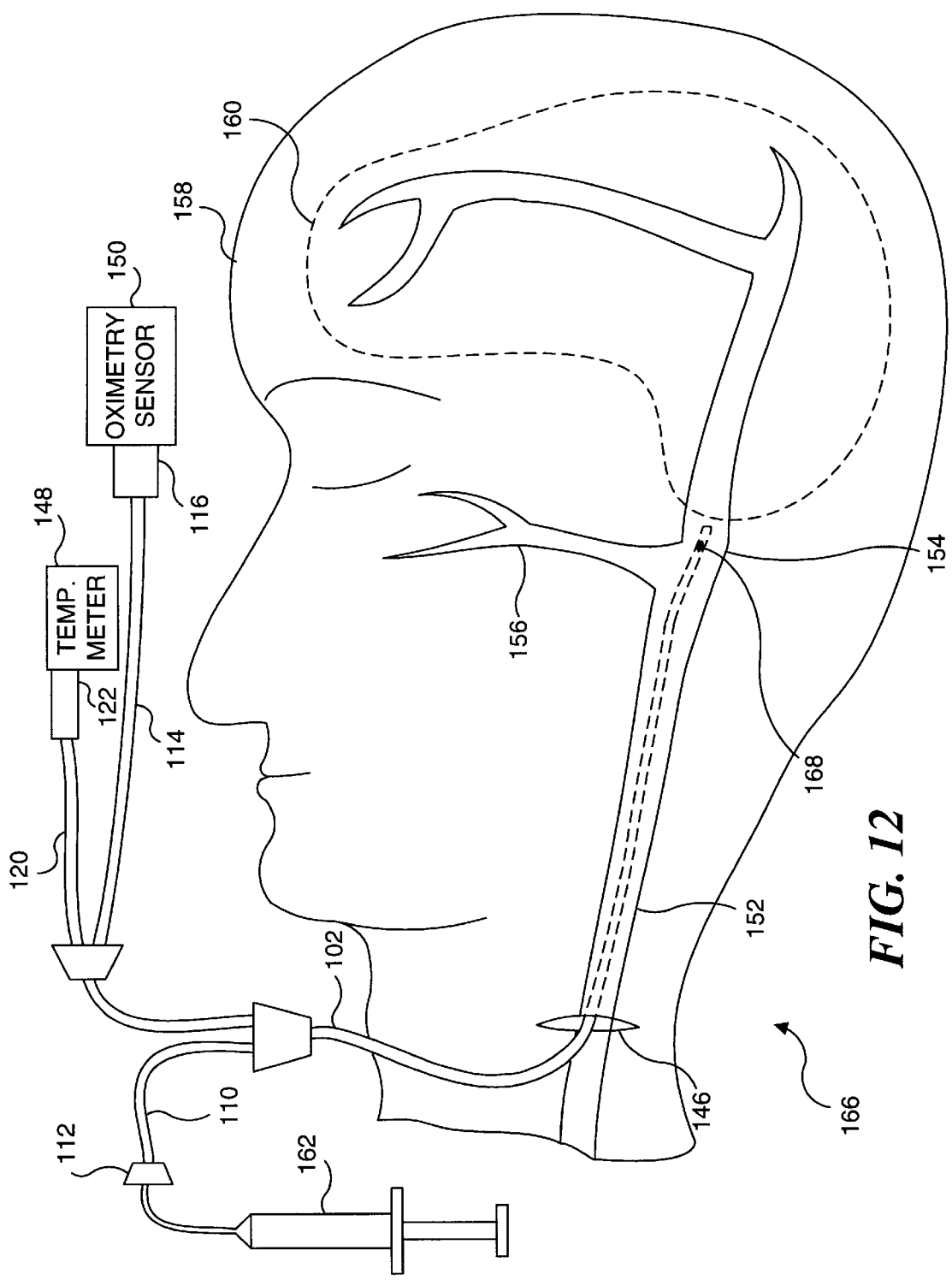
FIG. 12 is a schematic drawing illustrating the distal end of the oximetry catheter disposed at the jugular bulb in the interior jugular vein of the patient.

In FIG. 12, a schematic overview 166 shows the distal end of catheter 102 disposed at jugular bulb 154. Guide wire 144 has been removed from fitting 112, and a syringe 162 coupled to the fitting. Syringe 162 is used to inject a saline or another physiologically inert solution into lumen 140. The injected solution flows from lumen 140 (FIG. 2) into lumen 137 (FIG. 6) and out port 130 (FIGS. 7 and 8). The solution inhibits the coagulation of blood at distal end 125a and distal end 125b at the distal end of catheter 102. In this way, the accuracy of the oxygen saturation measured by oximetry sensor 150 may be maintained for extended periods of time.

Temperature indicator 148 enables the distal end of catheter 102 to be precisely disposed at jugular bulb 154, since the venous blood temperature measurement will be slightly higher at this position than when the distal end is positioned at, or slightly below, facial vein 156. Furthermore, it is desirable to position the distal end of catheter 102 away from a wall of jugular bulb 154 so that the reflection of light emitted by distal end 125a from the wall back into distal end 125b is minimized, and the accuracy of the percentage of oxygen saturation is thereby improved. Although not shown in this Figure, the plurality of indicia 126 may also be employed to position the distal end of catheter 102 at jugular bulb 154.

Figure 13:
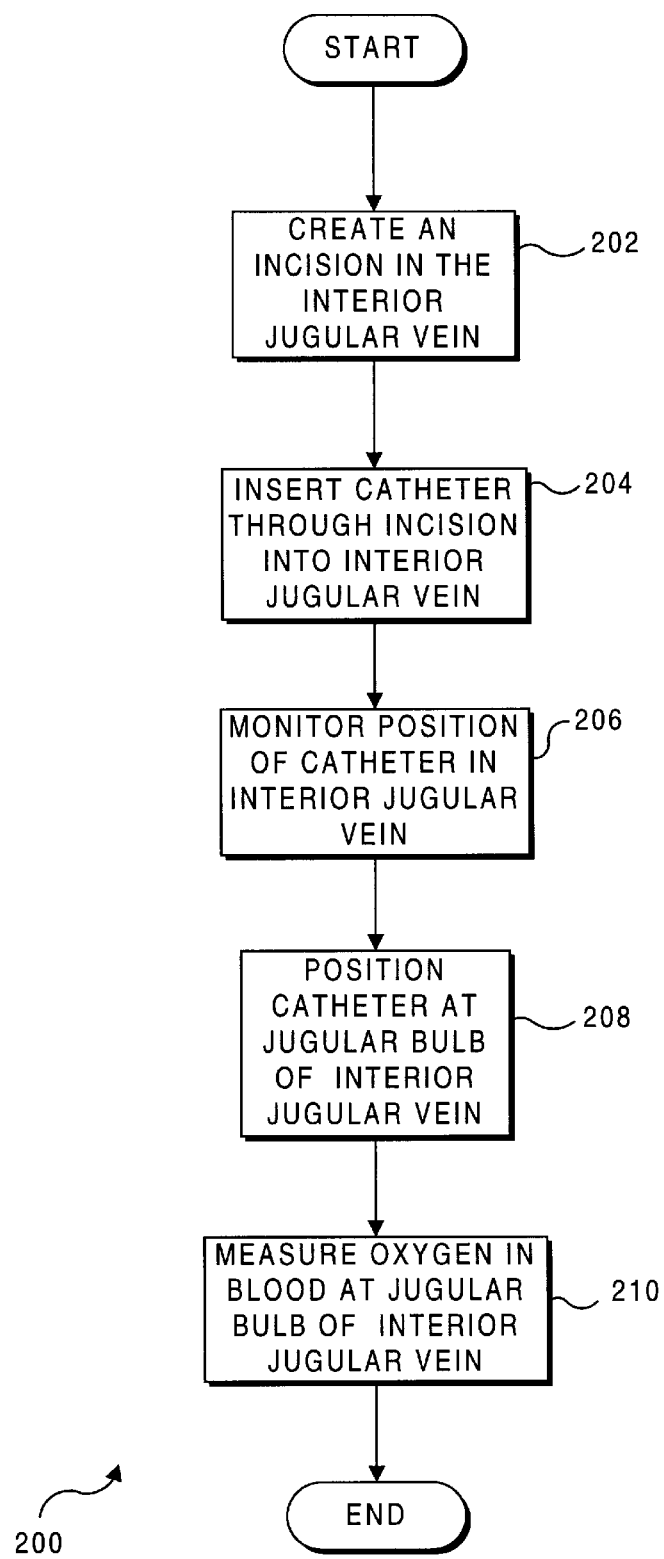
FIG. 13 is a logical block diagram listing the steps for determining the percentage of oxygen saturation in venous blood at the jugular bulb in the interior jugular vein of the patient.

With reference to FIG. 13, the steps employed to measure the percentage of oxygen saturation of hemoglobin in venous blood flowing from brain 160 through interior jugular vein 152 are listed. A block 202 indicates that the medical practitioner creates incision 146 in the neck of the patient to access interior jugular vein 152. Optionally, an introducer device may be positioned at incision 146 to improve access to interior jugular vein 152. A block 204 next indicates that the medical practitioner inserts catheter 102 through incision 146 into interior jugular vein 152. Prior to inserting catheter 102, the medical practitioner should preferably flush catheter 102 with a physiologically inert solution such as saline and insert guide wire 144 through fitting 112, advancing the guide wire along lumen 140 and into lumen 138. The distal end of guide wire 144 is positioned slightly back from port 130, adjacent the distal end of catheter 102.

A block 206 provides that catheter 102 (with guide wire 144 inserted) is threaded into interior jugular vein 152. The medical practitioner monitors the position of the distal end of catheter 102 by observing a change in the venous blood temperature displayed by temperature meter 148. Additionally, the medical practitioner may employ the plurality of indicia 126 disposed at periodic intervals along the exterior surface of the distal portion of catheter 102 for monitoring the distance that the distal end of the catheter has been advanced within interior jugular vein 152.

As noted in a block 208, the distal end of catheter 102 is positioned at jugular bulb 154. The temperature displayed by temperature meter 148 and/or the distance identified by indicia 126 may be employed to determine the positioning of the distal end of catheter 102 at jugular bulb 154. Also, when the medical practitioner experiences a slight resistance to the advance of catheter 102 at jugular bulb 154, the distal end of the catheter will normally be withdrawn approximately one centimeter back from the position at which the resistance was felt. At this point, catheter 102 should be precisely positioned at jugular bulb 154 and slightly above facial vein 156. In addition, the distal end of catheter 102 is positioned away from a wall of jugular bulb 154 so that light reflection from the wall is significantly reduced and the accuracy of the percentage of oxygen saturation determination is enhanced.

In a block 210, the percentage of oxygen saturation in hemoglobin for the venous blood flow at jugular bulb 154 is continuously monitored. The displayed value of oximetry sensor 150 enables the medical practitioner to determine in real time the percentage of oxygen saturation in the venous blood flowing from brain 160. As the blood supplied to brain 160 decreases, the brain absorbs more oxygen and the percentage of oxygen saturation in the hemoglobin for the venous blood will decrease.

The preferred embodiment of the present invention described above determines the percentage of oxygen saturation in hemoglobin at a level of accuracy that differs no more than 10 percent from that measured in an ex vivo laboratory test. This level of accuracy is partially achieved by providing a catheter in which the disposition of distal end 125a and distal end 125b in the cross-sectional center ensures that at least the distance between the periphery of either of these optical fiber distal ends and the periphery of the distal end of the catheter is at least 0.0200 inches. Further, the center-to-center distance between distal end 125a and distal end 125b is preferably between 0.0095 inches and 0.0105 inches. Also, the face of the distal end of catheter 102 is preferably maintained at least 0.020 inches away from the wall of the blood vessel. In this way, the amount of light reflected from the wall of the blood vessel is minimized, and the accuracy of the percentage of oxygen saturation determination is substantially improved. Thus, the medical practitioner using the present invention is not required to make repetitive in vivo calibrations to ensure the percentage of the oxygen saturation in blood is accurately determined.

Optionally, it may be desirable to reposition the distal end of catheter 102 in a blood vessel. Accordingly, guide wire 144 may be repeatedly inserted into lumen 138 so that the medical practitioner may reposition the distal end of catheter 102 at various locations in the blood vessel.

It is envisioned that catheter 102 may be coated with an anticoagulant, such as heparin, to prevent blood clotting along the surface of the catheter. It is further envisioned that oximetry sensor 150 may include an alarm to notify the medical practitioner when the percentage of oxygen saturation in venous blood has either risen above or fallen below predetermined values. In either case, oximetry sensor 150 will then indicate that a problem with the supply properly oxygenated blood to brain 160 exists.

Another application of the present invention is determining the percentage of oxygen saturation in hemoglobin for arterial blood flowing through an artery. When used for this purpose, catheter 102 is inserted into the artery and advanced to a position at which the percentage of oxygen saturation will be monitored.

It will be understood that the present invention is not limited to determining the percentage of oxygen saturation of blood flowing from the patient's brain. This invention can also be employed to determine the percentage of oxygen saturation for blood flowing through a small diameter blood vessel disposed in a different portion of the patient's body.

It is further contemplated that the optical transmitter and optical receiver used for monitoring the percentage of oxygen saturation in the patient's blood might be time or frequency multiplexed (light wavelength) to provide for more precise monitoring of the percentage of oxygen saturation.

Yet another application of the present invention is measuring the pressure of blood flowing past the distal end of catheter 102. Although all of the details are not shown in the Figures, a pressure monitoring system could be coupled to fitting 112. The pressure monitoring system would measure the pressure of the blood in the blood vessel through the fluid path provided by lumens 140 and 135. Also, another application of the present invention (not entirely shown in the Figures) would connect a blood sampling system to fitting 112. The blood sampling system could sample the blood flowing past the distal end of catheter 102 through the fluid path provided by lumens 140 and 135.

It is further envisioned that the distal end of catheter 102 may include a rounded edge 180 that is disposed along the periphery of the distal end, as shown in FIG. 8. When the user is positioning the distal end of catheter 102 inside the patient, rounded edge 180 will prevent the distal end from catching on tissue and/or the interior of a blood vessel. In the preferred embodiment, rounded edge 180 has an approximate radius of 0.005 inches.

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for monitoring a percentage of oxygen saturation in blood flowing through a blood vessel, comprising:
   (a) a flexible catheter having an elongated cylindrical shape and a diameter sufficiently small to enable the catheter to be advanced into the blood vessel as the blood is flowing through the blood vessel;
   (b) a pair of optical fibers disposed within the catheter and extending generally along the length of the catheter, from a point adjacent to a distal end of the catheter, one of said optical fibers being adapted for coupling to a transmitter and being used for conveying light from the transmitter, another of said optical fibers being adapted for coupling to a receiver and conveying reflected light to the receiver; and
   (c) an oxygen sensor for indicating the percentage of oxygen saturation in the blood flowing through the blood vessel, the oxygen sensor including the transmitter and the receiver and being coupled to the proximal end of the catheter, the optical fibers being generally centered about a central longitudinal axis of the catheter, to maximize a distance between each distal end of each optical fiber and a periphery of the catheter, so that reflection of light emitted from a distal end of said one optical fiber from a wall of the blood vessel, which would cause an error in the percentage of oxygen saturation determined by the oxygen sensor, is substantially reduced.

2. The apparatus of claim 1, further comprising a thermistor disposed adjacent to the distal end of the catheter, said thermistor being adapted to sense a temperature of the blood flowing past the catheter.

3. The apparatus of claim 2, further comprising leads disposed within the catheter and coupled to the thermistor, said leads extending proximally from the thermistor through the catheter and having proximal ends adapted to couple to a temperature indicator that displays a temperature of the blood.

4. The apparatus of claim 3, wherein the temperature of the blood is employed to determine a relative position of the catheter within the blood vessel.

5. The apparatus of claim 1, wherein the transmitter is coupled to a proximal end of said one optical fiber and adapted for transmitting light that is emitted out of the distal end of said one optical fiber into the blood flowing past the distal end of the catheter, and the receiver is coupled to a proximal end of the other optical fiber and adapted for receiving reflected light from blood flowing past a distal end of said other optical fiber disposed at the distal end of the catheter, an intensity of said reflected light being indicative of the percentage of oxygen saturation in the blood.

6. The apparatus of claim 5, wherein the receiver receives light that is reflected by hemoglobin in a red blood cell.

7. The apparatus of claim 5, wherein the oxygen sensor further comprises a meter that displays the percentage of oxygen saturation in the blood.

8. The apparatus of claim 1, wherein the oxygen sensor has an alarm that indicates a relationship between the percentage of oxygen saturation and a predetermined value.

9. The apparatus of claim 1, wherein the catheter is coated with an anti-clotting agent.

10. The apparatus of claim 1, further comprising a strain relief member extending along the length of the catheter, the strain relief member being flexible and resistant to longitudinal stretching.

11. The apparatus of claim 10, wherein the strain relief member comprises a polymer thread.

12. The apparatus of claim 1, wherein the catheter includes a lumen extending generally along the length of the catheter that is adapted to receive a guide wire, the guide wire being inserted into the lumen to make the catheter less flexible and thereby facilitate positioning the distal end of the catheter at a predetermined position in the blood vessel, said guide wire being retracted from the lumen when the catheter is at the predetermined position.

13. The apparatus of claim 12, wherein the lumen is adapted to enable the guide wire to be reinsertable into the lumen to enable the user to reposition the distal end of the catheter in the blood vessel.

14. The apparatus of claim 1, wherein the lumen is adapted to couple to a fluid supply, the fluid supply being coupled to the lumen to enable the catheter to be flushed with a fluid to inhibit the coagulation of blood at the distal end of the catheter.

15. The apparatus of claim 5, wherein each edge of the distal end of each optical fiber is disposed at least 0.020 inches from a periphery of the distal end of the catheter.

16. The apparatus of claim 5, wherein a center-to-center distance between the distal ends of the pair of optical fibers is less than or equal to 0.0105 inches.

17. The apparatus of claim 1, wherein the blood vessel comprises one of an artery and a vein.

18. The apparatus of claim 1, further comprising a plurality of indicia visible on an outer surface of the catheter, positioned at intervals along the length of the catheter.

19. The apparatus of claim 18, wherein the plurality of indicia are provided to indicate a length of the catheter that has been inserted into the blood vessel.

20. The apparatus of claim 1, wherein the distal end of the catheter has a rounded edge disposed along the periphery of said distal end of the catheter.

21. A catheter for monitoring a percentage of oxygen saturation in blood flowing through a blood vessel, comprising:
(a) a lumen disposed within the catheter and extending along a length of the catheter;
(b) a pair of optical fibers extending through the lumen to a distal end of the catheter;
(c) a proximal end of one of the pair of optical fibers being adapted to couple to an optical transmitter disposed at a proximal end of the catheter to convey light emitted by the optical transmitter to a distal end of said one of the pair of optical fibers, for emission therefrom into the blood; and
(d) a proximal end of the other of the pair of optical fibers being adapted to couple to an optical receiver disposed at a proximal end of the catheter to convey light reflected from hemoglobin in red blood cells in the blood, distal ends of the pair of optical fibers being disposed substantially at a center of the distal end of the catheter to maximize a distance between a periphery of the catheter and the distal ends of the pair of optical fibers, and thereby to reduce the light emitted from the distal end of said one of the pair of optical fibers that is reflected from a wall of the blood vessel so that the light reflection does not cause a substantial error in an accuracy with which the percentage of oxygen saturation in the blood flowing through the blood vessel is monitored.

22. A method for monitoring the percentage of oxygen saturation in blood flowing through a blood vessel, comprising the steps of:
(a) opening an incision in a body of a patient, the incision providing an access into the blood vessel;
(b) providing a catheter that includes an optical fiber sensing system, said optical fiber sensing system including a transmitting optical fiber and a receiving optical fiber, a distal end of the transmitting optical fiber and a distal end of the receiving optical fiber being disposed substantially at a center of a distal end of the catheter, to maximize a distance between each distal end of each optical fiber and a periphery of the catheter, so that reflection of light emitted from a distal end of said one optical fiber from a wall of the blood vessel, which would cause an error in the percentage of oxygen saturation determined by the oxygen sensor, is substantially reduced;
(c) inserting the catheter into the blood vessel through the incision;
(d) positioning the distal end of the catheter at a position in the blood vessel, away from a wall of the blood vessel; and
(e) monitoring a percentage of the oxygen saturation in the blood flowing through the blood vessel with the optical fiber oxygen sensing system.

23. The method of claim 22, further comprising the step of inserting an introducer device into the incision, the intrusion device providing a more defined access into the blood vessel for insertion of the catheter.

24. The method of claim 22, further comprising the step of flushing the catheter with a fluid flowing through the catheter and out the distal end of the catheter into the blood vessel, so that the clotting of blood on the optical fiber oxygen sensing system is inhibited by the fluid.

25. The method of claim 22, wherein the step of inserting the catheter into the blood vessel through the incision further comprises the step of inserting a guide wire into a lumen disposed within the catheter and extending along a length of the catheter, the guide wire reducing the flexibility of the catheter to facilitate guiding the catheter through the blood vessel.

26. The method of claim 22, wherein the step of positioning the distal end of the catheter further comprising the steps of:
(a) advancing the catheter into the blood vessel until resistance is sensed; and then
(b) moving the catheter back a predetermined distance away in the blood vessel.

27. The method of claim 26, wherein the predetermined distance is at least one centimeter.

28. The method of claim 22, wherein the step of positioning the distal end of the catheter comprises the step of determining a change in a temperature of the blood flowing past the distal end of the catheter, the change indicating the position of the distal end of the catheter in the blood vessel relative to a branch blood vessel.

29. The method of claim 22, wherein the step of positioning the distal end of the catheter comprises the step of monitoring a plurality of indicia disposed at periodic intervals along a length of the catheter to determine a length of the catheter disposed in the blood vessel.

30. The method of claim 22, further comprising the step of measuring the pressure of the blood flowing in the blood vessel through a lumen that is disposed in the catheter.

31. The method of claim 22, further comprising the step of sampling blood flowing in the blood vessel through a lumen that is disposed in the catheter.

* * * * *